United States Patent [19]
Plaut et al.

[11] Patent Number: 5,972,348
[45] Date of Patent: Oct. 26, 1999

[54] HELICOBACTER PYLORI NICKEL BINDING PROTEIN

[75] Inventors: Andrew G. Plaut, Lexington; Joanne V. Gilbert-Rothstein, Arlington; Andrew Wright, Lincoln, all of Mass.

[73] Assignee: New England Medical Center Hospitals Inc., Boston, Mass.

[21] Appl. No.: 09/115,032

[22] Filed: Jul. 14, 1998

Related U.S. Application Data

[62] Division of application No. 08/255,457, Jun. 8, 1994, Pat. No. 5,780,040.

[51] Int. Cl.$^6$ ............................................. A61K 39/02
[52] U.S. Cl. ........................................ 424/234.1; 435/7.32
[58] Field of Search ................................ 424/92, 234.1; 435/12, 7.32, 6; 800/2

[56] References Cited

U.S. PATENT DOCUMENTS

| | | | |
|---|---|---|---|
| 4,882,271 | 11/1989 | Evans et al. | 435/7 |
| 5,260,057 | 11/1993 | Cordle | 424/85.8 |
| 5,262,156 | 11/1993 | Alemohammad | 424/234.1 |
| 5,314,804 | 5/1994 | Boguslaski et al. | 435/12 |
| 5,527,678 | 6/1996 | Blaser et al. | 435/6 |
| 5,538,729 | 7/1996 | Czinn et al. | 424/234.1 |
| 5,567,594 | 10/1996 | Calenoff | 435/7.32 |
| 5,625,124 | 4/1997 | Falk et al. | 800/2 |
| 5,780,040 | 7/1998 | Plaut et al. | 424/234.1 |

FOREIGN PATENT DOCUMENTS 0329570  2/1989  European Pat. Off. .

OTHER PUBLICATIONS

Babler et al., Immun. Infekt., vol. 20, No. 3, issued Mar. 1992, pp. 103–106.
Best, L.M. et al., "Serological Detection of *HelicobacterPylori* Anitbodies in Children and Their Parents", 1994, J. Clin. Microbiology, 32:1193–96.
Collins et al., Molecular Microbiology, vol. 9, No. 5, issued Sep. 1993, pp. 907–913.
Creighton, T.E., "Proteins, Structures and Molecular Properties", published 1984, pp. 28–53.
Cussac, V., et al., "Expression of *Helicobacter Pyori* Urease Genes in *Escherichia Coli* Grown Under Nitrogen–Limiting Conditions", 1992, J. Bacteriology, 174:2466–2473.
Gilbert et al., Infection & Immunity 63:2682–2688, 1995.
Hawtin et al., FEMS Microbiol Lett 77:51–54, 1991.
Houghten et al., Vaccine 86 Relative Importance of Position & Individual Amino Acid Residues in Poptide Antigen Antibody Interactions: Implication in the Mechanisms of Antigenic Draft & Antigenic Shift pp. 21–25.
Hu, L.T., et al., "Purification of Recombinant *Helicobacter Pylori* Urease Apoenzyme Encoded by ureA and ureB", 1992, Infection and Immunity, 60:2657–2666.
Jung et al., The Seoul Journal of Medicine, col. 31, No. 4, issued Dec. 1990, pp. 231–246.

Lee, M.H., et al., "Klebsiella Aerogenes Urease Gene Cluster: Sequence of ureD and Demonstration that Four Accessory Genes (ureD, ureE, ureF, and ureG) Are Involved in Nickel Metallocenter Biosynthesis", 1992, J. Bacteriology, 174:4324–4330.
Lee, M.H. et al., "Purification and Characterization of Klebsiella Aerogenes UreE protein: A Nickel–binding Protein that Functions in Urease Metallocenter Assembly", 1993, Protein Science, 2:1042–1052.
Lelwala–Guruge et al., Scan. J. Infect. Dis., vol. 24, No. 4, issued 1992, pp. 457–465.
Mobley et al., Microbiological Reviews, vol. 53, No. 1, issued Mar. 1989, pp. 85–108.
Mulrooney, S., et al., "Sequence of the Klebsiella Aerogenes Urease Genes and Evidence for Accessory Proteins Facilitatin Nickel Incorporation", 1990, J. Bacteriology, 172:5837–5843.
Nagata et al., Infection & Immunity 60: 4826–4831, 1992.
Owen, R.J., et al., "Comparison of PCR–Based Restriction Length Polymorphism Analysis of Urease Genes with rRNA Gene Profiling for Monitoring Helicobacter Pylori Infections in Patients on Triple Therapy", J. Clinical Microbiology, 32:1203–10.
Park, I.S., et al., "In vitro Activation of Urease Apoprotein and Role of UreD as a Chaperone Required for Nickel Metallocenter Assembly", 1994, Proc. Natl. Acad. Sci. USA, 91:3233–3237.
Park, I.S., "Site–directed Mutagenesis of Klebsiella Aerogenes Urease" Identification of Histidine Residues that Appear to Function in Nickel Ligation, Substrate Binding, and Catalysis, 1993, Protein Science, 2:1034–1041.
Rappuoli et al., Journal of Gastroenterology and Hepatology 5:576–598.
Sriwanthana, B., et al., "Proteus Mirabilis Urease: Histidine 320 of UreC is Essential for Urea Hydrolysis and Nickel Ion Binding within the Native Enzyme", 1993, Infection and Immunity, 61:2570–2577.
Stacey et al., Eur. J. Clin. Microbiol. Infect. Dis., vol. 9., No. 10, issued Oct. 1990, pp. 732–737.
Suerbaum et al., Abstracts of the 93rd Gen. Meeting of the American Society for Microbiology, D–182, p. 127.
Suerbaum et al., Molecular Microbiology 14:959–974 1994 (Abstract only).
Sunderman, F.W., "Lipid Peroxication as a Mechanism of Acute Nickel Toxicity", 1987, Toxicological and Environmental Chem. 15:59–69.

(List continued on next page.)

*Primary Examiner*—James C. Housel
*Assistant Examiner*—Ginny Allen Portner
*Attorney, Agent, or Firm*—Fish & Richardson, P.C.

[57] ABSTRACT

The application discloses a nickel binding protein and its encoding DNA isolated from *Helicobacter pylori*. This organism is the primary cause of chronic gastritis and ensuing peptic ulcers, and has been implicated in stomach cancer. The nickel binding protein is useful to inhibit assembly of active ureases, the enzymes responsible for the pathogenic features of the bacterium. Potential uses include as a vaccine, a diagnostic, a drug target, and a therapy in itself.

6 Claims, 2 Drawing Sheets

OTHER PUBLICATIONS

Van Zwet, A.A., et al., "Use of PCR with Feces for Detection of *Helicobacter Pylori* Infections in Patients", 1994, 32:3146–1348.

Von Wulffen et al., Zentrablatt Fuer Bakteriologie, vol. 280, No. 1–2, issued 1993, pp.203–213.

Walsh et al., Biochemistry, vol. 26, No. 16, issued Aug. 11, 1987, pp. 4901–4906.

Dunn, B. et al., "Identification and Purification of a CPN60 Heat Shock Protein Homolog from *Helicobacter–Pylori*" Infection and Immunity 60 (5), 1992, 1946–1951.

Evans, D.J., Jr, et al., "Urease–Associated Heat Shock Protein of *Helicobacter–Phlori*", Infection and Immunity, 60 (5), 1992, 2125–2127.

Andersen et al (1992), J. Clin. Microbiol, Jul. vol. 30(7), pp. 1743–1751.

Andersen et al (1995) Mar. Clin. Daig. Lab. Immunol., vol. 2(2), pp. 156–159.

Dunn et al (1989) Jun. vol. 57(6), Infect Immun., pp. 1825–1833.

Evans et al, 1991, Microbial Path., vol.10, pp.15–26.

Engstrand, L. (1992), UPsala J, Med. Sci., vol.97(1) pp. 1–26.

Stacey, A. R. et al, Eur. J. Clin. Microbiol. Infect. Dis. Oct. 1990, vol. 9(10), pp. 732–737.

Suerbaum, S. et al, Mol. Microbiol, 1994, vol. 14(5), pp. 959–974.

Landini, M. P. et al, Microbiologica, (PAVIA), vol. 12(3), 1989, pp. 181–188.

Labigne, A. et al., Mar. 1991, vol. 173(6), J. Bact., pp. 1920–1931.

von Wulffen, H. et al., Aug. 1988, vol. 7(4), Eur. J. Clin. Microbiol., pp. 559–565.

Sauerbaum, S. et al., May 19, 1993, 93rd ASM General Meeting, Session 249, #D182 (abstract).

ATG GCA CAC CAT GAA GAA CAG CAC GGC GGT CAT CAC CAT CAC CAC
Met Ala His His Glu Glu Gln His Gly Gly His His His His His
            ⎿___________a___________⏌   ⎿______b______
1                    5                       10              15

CAC ACA CAC CAC CAC TAT CAC GGC GGT GAA CAC CAC CAT CAC CAC
His Thr His His His Tyr His Gly Gly Glu His His His His His
                        20                      25              30

CAC AGC TCT CAT GAA GAA GGT GGT TGT TGC AGC ACT AGC GAT AGT CAT
His Ser Ser His Glu Glu Gly Gly Cys Cys Ser Thr Ser Asp Ser His
                35                      40                  45

CAT CAA GAA GAG GGT TGC TGC CAC GGG CAT CAC GAG TAA
His Gln Glu Glu Gly Cys Cys His Gly His His Glu
        ⏋⎿______________c______________
50              55                  60

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO:1:

Met Ala His His Glu Glu Gln His Gly Gly His His His His His
    1               5                   10                  15

His Thr His His His His Tyr His Gly Gly Glu His His His His
                    20                  25                  30

His Ser Ser His His Glu Glu Gly Cys Cys Ser Thr Ser Asp Ser His
                    35                  40                  45

His Gln Glu Glu Gly Cys Cys His Gly His His Glu
                    50                  55                  60

(2) INFORMATION FOR SEQ ID NO:2:

(i) SEQUENCE CHARACTERISTICS:
        (A) LENGTH: 710 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

GATCTAAACG ACAGCTTGGA CCGCGCTAAA AAACTTTTAA AACTTTTAAA CGGCATTAAA        60

TCCAAAGTGA ACTTGATTTT ATTCAACCCG CATGAAGGCT CTAAATTTGA GCGCCCCAGT       120

TTAGAGAGTG CCAGAATGTT TGCGGATTTT TTAAACTCTA AAGGCTTATT ATGCACCATT       180

AGAGAGTCTA AAGCCTTGGA TATTGAAGCG GCTTGCGGGC AATTGAGGGA GAAAAAACTC       240

TCCCAACAAA TTTGAAAACT TTTTTTGTGG TGTTTGTCTT TTTTCTAATG GGGGTGTTGG       300

TTTTAATCAA GCGATAATTC AAAATTTAGG GGATATGGAT TAAAAATTAG CACTAAATTT       360

TCTTTCATTA ACAATTAATT AGATTTTATA TTGTAGAATG GAATTCTAGC CAGTGAGCTA       420

GAATTTAAAT TTTTAATCAA AGGAGTCATC ATGGCACACC ATGAAGAACA GCACGGCGGT       480

CATCACCACC ATCACCACCA CACACACCAC CACCACTATC ACGGCGGTGA ACACCACCAT       540

CACCACCACA GCTCTCATCA TGAAGAAGGT TGTTGCAGCA CTAGCGATAG TCATCATCAA       600

GAAGAGGGTT GCTGCCACGG GCATCACGAG TAATATCGGT GTGGCTAGGG GCAACTTGAC       660

TTGTCTCTAG CGTTTTAATT TTATTTTCTC TCAAATTTAT TCAATCAATT                 710

(2) INFORMATION FOR SEQ ID NO:3:

(i) SEQUENCE CHARACTERISTICS:
        (A) LENGTH: 183 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

-continued

```
ATGGCACACC ATGAAGAACA GCACGGCGGT CATCACCACC ATCACCACCA CACACACCAC        60

CACCACTATC ACGGCGGTGA ACACCACCAT CACCACCACA GCTCTCATCA TGAAGAAGGT       120

TGTTGCAGCA CTAGCGATAG TCATCATCAA GAAGAGGGTT GCTGCCACGG GCATCACGAG       180

TAA                                                                    183
```

HELICOBACTER PYLORI NICKEL BINDING PROTEIN

RELATED APPLICATION INFORMATION

This application is a divisional of application Ser. No. 08/255,457, filed Jun. 8, 1994 now U.S. Pat. No. 5,780,040.

This invention was made with Government support under grant #DE09677 awarded by the Public Health Service. The Government has certain rights in the invention.

BACKGROUND OF THE INVENTION

The field of the invention is diagnosis, prophylaxis, and treatment of gastric disease and nickel-related disorders; and non-clinical nickel detoxification The invention also relates to the bacterium *Helicobacter pylori*.

The bacterium *Helicobacter pylori* was first isolated from human gastric mucosa in 1983, and was originally identified as a member of the genus Campylobacter (either *C. pylori* or *C. pyloridis*; Warren and Marshall, Lancet i:1273, 1983; Marshall and Goodwin, *Int. J. Syst. Bacteriol.* 37:68, 1987). *H. pylori* is recognized as a pathogen, and is a major cause of chronic gastritis, inflammation of the gastric mucosa, and peptic ulcers. It can also contribute to the development of gastric cancer (for review, see Sipponen et al., "Histology and Ultrastructure of *Helicobacter pylori* Infections: Gastritis, Duodenitis, and Peptic Ulceration, and Their Relevant Precancerous Conditions", in *Helicobacter pylori: Biology and Clinical Practice* 37, Goodwin and Worsley, eds., 1993).

*H. pylori* is able to survive in the highly acidic environment of stomach at least in part due to its high urease activity, which may raise the pH of the local environment by hydrolyzing endogenous urea into ammonia and carbon dioxide. The ammonia component affects the pH, and its local accumulation is thought to have a directly toxic effect on nearby mucosa.

Urease activity is one of the principal properties of the bacterium. The urease of *H. pylori* has been well characterized, and consists of a high molecular weight (550 kDa) multimeric enzyme. There are two primary subunits, UreA (66 kDa) and UreB (29.5 kDa), and these combine to make a larger subunit, six of which ultimately combine to form the intact protein. *H. pylori* urease enzyme is homologous to ureases of other bacterial species, and to plant ureases (e.g., jackbean).

All ureases studied to date contain nickel, and *H. pylori* urease has been shown to contain 5.21 nickel atoms per molecule. *H. pylori* urease activity depends on the availability of nickel ion in the enzyme active site; the cloned enzyme in *E. coli* that yields high levels of protein only has urease activity if a source of nickel ion (typically in the form of $NiCl_2$) is provided in the *E. coli* growth medium. This nickel must be present during enzyme synthesis, and cannot be added after the protein is fully synthesized. Also, histidine or cysteine, amino acids that actively chelate nickel ions, prevent nickel uptake or entry into the cloned urease protein expressed in *E. coli*. Thus, recombinant urease activity is low if the cells are cultured in a rich medium which contains much histidine and cysteine.

No uptake mechanism for nickel by *H. pylori* or by the structural urease subunits has been defined. Accessory genes near the urease structural genes in several microorganisms have been postulated to involve nickel uptake, such as a UreD accessory gene product in *Aspergillus nidulans*, or the histidine-rich UreE gene products in *Klebsiella aerogenes* and *P. mirabilis*, but none of this has been proven. Separate mechanisms for uptake of nickel by the organism and incorporation of nickel by the urease may exist.

SUMMARY OF THE INVENTION

In general, the invention features a substantially pure nickel binding protein of Helicobacter containing the amino acid sequence SEQ ID NO: 1, and having a monomeric molecular weight of about 14 kDa based on migration in polyacrylamide gel electrophoresis (PAGE). This protein is further characterized by binding non-covalently to nickel at pH values between 4.5 and 8, optimally between pH 6–8.

In another aspect, the invention features biologically active fragments of the nickel binding protein. By "biologically active fragment" is meant a fragment which can exert a physiological effect of the full-length, naturally-occurring protein (e.g., binding to its biological substrate, causing an antigenic response, etc.).

Also featured are polypeptides that are substantially identical to SEQ ID NO 1. By "substantially identical," it is meant an amino acid sequence which differs only by conservative amino acid substitutions, for example, substitution of one amino acid for another of the same class (e.g., valine for glycine, arginine for lysine, etc.) or by one or more non-conservative amino acid substitutions, deletions, or insertions located at positions of the amino acid sequence which do not destroy the biological function of the polypeptide; this includes substitution of alternative covalent peptide bonds in the polypeptide. By "polypeptide" is meant any chain of amino acids, regardless of length or post-translational modification (e.g., glycosylation or phosphorylation), and can be used interchangeably with the term "protein".

The invention also features fragments of the nickel binding protein which are antigenic. The term "antigenic," as used herein, refers to a fragment of the protein which can induce a specific immunogenic response; e.g., an immunogenic response which yields antibodies which specifically bind to the nickel binding protein, or induces cytotoxic lymphocytes. The fragments are preferably at least eight amino acids in length. In one preferred embodiment, the fragment includes the nickel binding domain of the nickel binding protein. By "domain" is meant the region of amino acids in the protein directly involved in the binding of nickel ions. The nickel binding proteins of the invention can be of natural or recombinant origin.

In another aspect, the invention features a nucleic acid sequence (SEQ ID NOs: 2 and 3) encoding the nickel binding protein, its degenerate variants, or a portion thereof, not less than 24 contiguous nucleotides in length. By "degenerate variants" is meant any nucleotide sequence, even if different from the natural sequence because of the degeneracy of the genetic code, that encodes the nickel binding protein of the invention, or a substantially identical polypeptide.

The invention also features antibodies which bind specifically to the protein or fragments of the invention.

Another aspect of the invention features a method of detecting a Helicobacter infection in a patient whereby a biological sample (e.g., serum, gastric secretion, or biopsy) is taken from the patient and tested for the presence of Helicobacter.

In preferred embodiments, antibodies that bind to the *H. pylori* nickel binding protein are detected using nickel binding protein or an antigenic fragment thereof as the substrate (e.g., by Western blotting). The presence of such antibodies in the patient will be indicative of an infection by Helicobacter. In other embodiments, detecting infection can be achieved by detecting the presence of the nickel binding protein itself, or by detecting the presence of DNA encoding the nickel binding protein (e.g., by PCR amplification or dot-blotting).

The invention also features a method of binding free nickel ions in a patient for therapeutic (e.g., to treat peptic ulcers, gastritis, or nickel toxicity) or prophylactic (e.g., to prevent peptic ulcers or gastritis) purposes by administering to the patient the nickel binding protein of the invention or a nickel binding domain of the protein, preferably by oral or systemic administration.

The invention also features a method of preventing or ameliorating gastroenteric tissue damage resulting from infection by a pathogenic nickel-obligate bacterium such as Helicobacter in a patient. The method involves administering to the patient specific antibodies which bind the nickel binding protein of the invention, thus binding and neutralizing the pathogenic bacteria in the host.

The invention also features a method to remove nickel ions from aqueous solutions by contacting the solution with a protein or soluble fragment of the invention to form metal-protein complexes, which are then removed from the solution. By "aqueous solution" is meant any liquid miscible in water which can be titrated to a pH in the range of 4–8. Such solutions include aqueous laboratory wastes, e.g., those containing radioactive isotopes such as $^{63}$Ni.

Another feature of the invention is a method of screening compounds for their potential use as therapeutics by assaying their ability to interact with the nickel binding protein or fragments of the invention. This method involves combining the compound to be tested with the protein or fragment and then assaying for nickel binding ability by contacting the protein with a nickel-linked resin and determining if the protein binds the nickel.

The invention also features a method of vaccinating a patient against infection by Helicobacter. This method entails administering to the patient the protein or fragments of SEQ ID NO 1 in a suitable excipient an amount to elicit an immunogenic response in the patient (e.g., production of antibodies, stimulating cytotoxic lymphocytes).

Another feature of the invention is a therapeutic method designed to mitigate gastric tissue damage by inhibiting production (via transcriptional or translational mechanisms) of the nickel binding protein or DNA of the invention. The method entails administering to a patient infected with Helicobacter antisense molecules to the DNA of the invention. By "antisense" is meant a molecule from 10 nucleotides or larger that is the reverse complement of a portion of the coding strand of the double stranded DNA of the invention.

The invention has advantages over prior diagnostic and preventive methods, and presents opportunities to develop novel therapeutics and diagnostics for a variety of nickel-related maladies, most notably *Helicobacter pylori* infection and nickel toxicity.

For instance, there are tests currently available which are able to diagnose *H. pylori* infection. These rely on an assay for urease activity. The instant invention improves upon these methods, because it is easier to obtain a serum sample for testing by the method of the invention than it is to obtain usable gastric tissue samples.

The nickel binding protein of the invention has other uses as well, such as for a vaccine to prevent *H. pylori* infection; or as a therapeutic agent in the case of such infection, to compete with *H. pylori* ureases to take up free nickel ions in the mucosa, rendering the assembled ureases less active. Alternatively, antibodies to the nickel binding protein can be used to inhibit incorporation of nickel into the ureases of Helicobacter. Additionally, the polypeptide or nickel binding fragments can be used systemically as a detoxifying agent for binding excess nickel ions (e.g., in cases of nickel toxicity).

Other features and advantages will be apparent from the following detailed description thereof, and from the claims.

DETAILED DESCRIPTION

*H. pylori* requires nickel ions during synthesis of urease in order to produce an active enzyme. There is disclosed herein a previously unknown, highly expressed nickel binding protein of Helicobacter that shows no significant homology to known nickel binding urease accessory genes. The protein was selectively isolated by adsorption of Helicobacter proteins onto insolubilized nickel ions in the form of an absorbent resin (Ni-NTA resin; Qiagen Inc., USA). A corresponding DNA clone has been identified and sequenced. This DNA is transcribed in abundance in cultured samples of *H. pylori*, and is probably used by the organism to sequester free nickel from the local environment, or in a functional step of assembling active urease. Due to its abundance, it is an excellent target for diagnostic and interventional applications for *H. pylori* infections in a human patient. Detailed descriptions of how to make and use the invention follow.

Culture of *Helicobacter pylori*

*Helicobacter pylori* strains were cultured in one of three ways:

1) Inoculation and incubation at 37° C. using standard techniques on sheep blood agar plate (Campyagar Skirrow, from Difco, Inc.) supplemented with 10% sheep blood and antibiotics (vancomycin, polymyxin, and trimethoprim).

2) Biphasic culture method, which entails overlaying a Campyagar-like plate with ten ml liquid Brucella broth supplemented with 0.1–0.2% cyclodextrin. Cells are added to the plate, and it is slowly shaken during culture 37° C. under microaerophilic conditions in a CampyPak (Becton Dickinson Microbiology Systems).

3) Cells are grown in Brucella broth with 0.1–0.2% cyclodextrin and antibiotics, also in microaerophilic conditions in a torsion jar.

Using all culture methods, the nickel binding protein was produced in comparable amounts.

Harvesting of cells and isolation of protein

Cells were obtained from agar plate cultures by scraping and eluting with phosphate buffered saline (PBS). Cells were then centrifuged (5,000 RPM) and washed once with PBS. From liquid cultures, cells were centrifuged down, and washed once with PBS.

Bacteria in the centrifuged pellet were resuspended in buffer B (8M urea, 10 mM Tris-HCl, 100 mM sodium phosphate. Solution adjusted to pH 8.2), which lyses the cells. The insoluble material from cell lysis was pelleted by centrifugation and the supernatant (containing the Helicobacter proteins and DNA) was re-centrifuged to ensure complete removal of particulate matter. To the clear supernatant was added 15 µl Ni-NTA resin (Qiagen, Inc., USA). This resin allows metal chelate affinity chromatography, and is nitrilo-tri-acetic acid charged with nickel ion ($Ni^{2+}$)—hence Ni-NTA. In this system, NTA binds to four of the six ligand binding sites in the coordination sphere of the $Ni^{2+}$ ion, leaving two sites free to interact with the nickel binding protein. This absorbent resin is in common use for another purpose, the isolation of proteins cloned by the Qiagen system, which involves attaching a 6xHis tail to the recombinant protein of interest and isolating by affinity binding to the Qiagen resin.

The mixture was slowly mixed by end-over-end shaking (10 oscillations per minute) for thirty minutes at room temperature to allow binding of nickel binding proteins to the resin. The resin was then settled by centrifugation, and washed four times with buffer C (the same as buffer B, above, but adjusted to pH 6.3). This treatment elutes proteins with a low binding affinity for the resin (it should be noted that similar methodology was attempted to purify the accessory urease protein ureE in Klebsiella, with no results). Supernatants containing the unwanted proteins were discarded. The nickel binding protein was released from the resin by resuspending the almost dry resin in buffer C that contained 0.1M EDTA, and adding SDS-PAGE sample buffer. This mixture was then boiled 7 min., the insoluble resin, depleted of nickel binding proteins, was removed by centrifugation. The supernatant containing the nickel binding protein was applied to 15% SDS-PAGE gels and electrophoresed under reducing conditions. The gel was stained with Coomassie Blue to identify the protein.

Protein at this point was highly concentrated and purified, but could have contained trace amounts of other, unidentified proteins. To fully isolate the protein for amino acid analysis, it was cut from the unstained gel, leaving other trace proteins behind. The protein was localized using typical molecular weight markers as a guide. It was then eluted by electroelution: the gel slice containing the nickel binding protein was put into Tris/glycine buffer and placed in dialysis tubing with a 3500 kDa cutoff. Protein was electroeluted from the gel for two hours at 4° C. and 100 volts. Following this, the dialysis tubing was opened at one end, the gel pieces removed, and the fluid containing the protein was dialyzed against 0.05% SDS/5.0 mM ammonium bicarbonate-$HCO_3$ overnight at 4° C., with several changes of dialysate.

The material was then removed from the dialysis tubing, placed in microfuge centrifugation tubes, and concentrated by evaporation in a SpeedVac until the volume was reduced to 50 µl in each tube. 450 µl acetone was then added for each 50 µl protein solution to precipitate the protein; this precipitation was held at −20° C. overnight. The precipitated protein material was then centrifuged, rinsed with acetone, recentrifuged, and the acetone was removed by air drying. Precipitate was then resuspended in 50 µl of a solution containing 8M urea and 0.4M ammonium bicarbonate, pH 8.0. Five µl of this solution was placed onto Immobilon P membrane previously wetted with methanol, then water. This membrane, with the adherent protein, was washed five times with water and used for amino acid analysis.

Amino acid analysis

Amino acid analysis of the nickel binding protein purified from H. pylori as described above is shown in Table 1 below. The histidine content was found to be 30 mole %.

TABLE 1

Amino acid analysis of Leone strain of Helicobacter pylori nickel binding protein.

| Peak # | Amino Acid | Picomoles | Mole Percent |
|---|---|---|---|
| 1 | Asp + Asn | 208.25 | 4.71 |
| 2 | Glu + Gln | 727.07 | 16.43 |
| 3 | Ser | 491.31 | 11.10 |
| 4 | Gly | 689.17 | 15.57 |
| 5 | His | 1326.95 | 29.98 |
| 6 | Arg | 69.38 | 1.57 |
| 7 | Thr | 179.65 | 4.06 |
| 8 | Ala | 122.36 | 2.76 |
| 9 | Pro | 69.64 | 1.57 |
| 10 | Tyr | 101.65 | 2.30 |
| 11 | Val | 83.78 | 1.89 |
| 12 | Met | 24.51 | 0.55 |
| 13 | Cys | 22.98 | 0.52 |
| 14 | Ile | 52.08 | 1.18 |
| 15 | Leu | 120.7 | 2.71 |
| 16 | Phe | 44.52 | 1.01 |
| 17 | Lys | 92.58 | 2.09 |
| TOTAL | | 4425.95 | |

Molecular weight, based on migration in SDS-PAGE gel, was 14 kDa when compared to standard molecular weight markers. This molecular weight is for the unitary polypeptide, and thus if the nickel binding protein is a hetero- or homopolymer, then 14 kDa is the subunit size. The single subunit has the capacity to bind nickel alone, as the purification process demonstrates.

Figure 1:
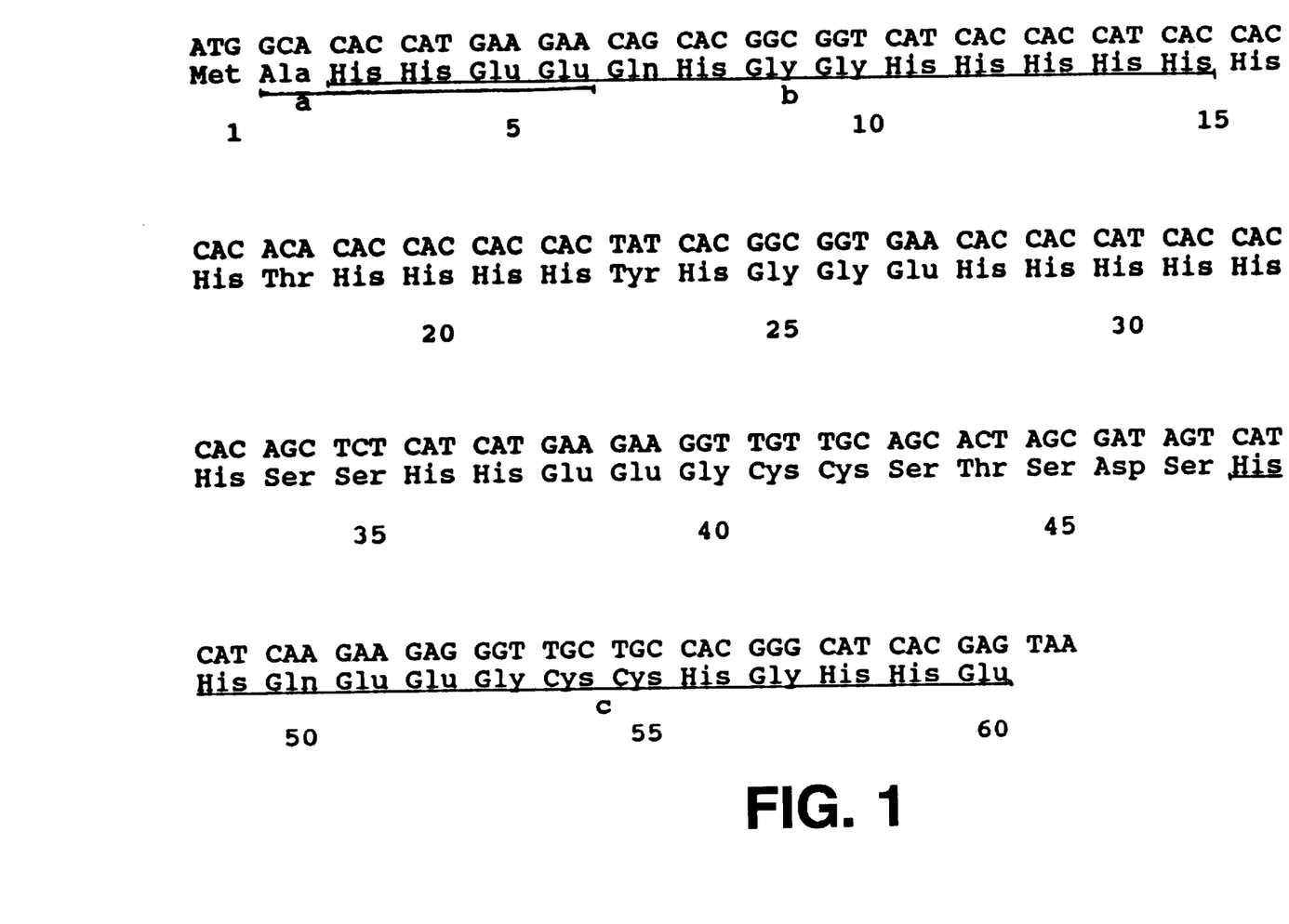
FIG. 1: Nucleic acid and amino acid alignment of the nickel binding protein. Underlined regions are tryptic fragments which were sequenced. a) is the N terminal sequence of the undigested nickel binding polypeptide (AHHEE); b) is tryptic peak 37 (_HHEEQHGGHHHHH_); c) is tryptic peak 14 (T_HHQEEG_(S)HGHHE).

The purified protein was subjected to amino terminal analysis, but was found to be blocked. Tryptic digests of the protein were used to gain access to interior residues. The reduced and alkylated protein was digested with modified trypsin (Boehringer Mannheim, Corp.), and fragments were separated by HPLC. Peaks were identified, and three fragments were subjected to Edman-type amino terminal analysis. The fragments sequenced are shown in FIG. 1.

This nickel binding protein has been found in all of the ten strains of H. pylori that have been isolated from different patients in the US and Japan. A protein of somewhat broader distribution on gels, but of approximately the same size, was found in two strains of H. mustelae obtained from ferrets.

H. pylori strains passaged approximately fifteen times in liquid culture continue to express the nickel binding protein in abundance. Thus, a convenient source of the intact wild type protein is available for use in all aspects of the invention.

Isolation of DNA clones

A genomic DNA library was constructed in a plasmid vector. *E. coli* were transformed with the DNA-containing plasmids, grown under selection, and allowed to express polypeptides. Colonies were probed for expression of the nickel binding polypeptide by modified Western protocol, using as a primary antibody the human antibody specific for the polypeptide.

Colonies were blotted onto nitrocellulose and lysed over filter paper soaked in 5% SDS. The membranes were baked at 100° C. for 15 minutes and subsequently incubated in 5% BSA/PBS containing DNAse and PMSF for 1 hr. The membranes were washed, placed in a transfer assembly, and electrophoresed for 1 hr. at 50V in a Tris/glycine/methanol buffer. The membranes could then be probed with specific antibody.

To prepare specific antibody, nickel binding polypeptide, purified using Ni-NTA, was electrophoresed on 15% SDS polyacrylamide gels, and electroblotted to Immobilon P membranes. The membranes were blocked with a PBS/1% BSA solution and then incubated with serum from a patient who tested positive for Helicobacter infection by ELISA assay. After a 3 hr. incubation at room temperature, the membranes were washed extensively with PBS/0.5% Tween 20. Specific antibody was eluted from the membranes using 0.1M glycine buffer at pH 2.6. The eluate was then titrated to a neutral pH using 1M Tris pH 8.

Sigma anti-human IgG alkaline phosphatase conjugate was used as a secondary antibody, and blots were developed with chromogenic phosphatase substrate.

Approximately 6000 colonies were screened, and 10 potentially positive clones were identified and isolated. Two clones were subsequently purified. Clone #1 has a 710 bp fragment of Helicobacter DNA, which was sequenced by the dideoxy chain termination method as known in the art (Sequenase 2, USB). The deduced amino acid sequence (SEQ ID NO. 1) of the nickel binding protein encoded by the cloned DNA (SEQ ID NO: 3) is shown in FIG. 1.

Protein Expression

The cloned DNA can be inserted into an expression vector which is then used to transform a host cell, e.g., *E. coli*, to produce recombinant nickel binding protein. Expression techniques are well known to those skilled in the art.

Production of Antibodies

The nickel binding protein or antigenic fragments thereof can be used to produce antibodies using conventional techniques. If antigenic fragments are to be used, they can be made using similar recombinant techniques as above, by inserting only the portion of DNA (24 or more nucleotides) encoding the amino acids of interest into a vector (e.g., prior to transformation of competent bacterial cells). Alternatively, the entire protein, whether recombinant or wild type, can be digested with specific proteases to obtain antigenic fragments of 8 or more amino acids.

Antisera can be generated by using either recombinant or wild-type purified protein as an immunogen according to methods well known in the art. Antisera are collected and screened for specificity using known methods.

Naturally occurring antisera have been collected from human patients infected with *H. pylori*, and antibodies to the nickel binding protein of the invention have been isolated following the methods of Hall et al. (*Nature* 311:379, 1984).

Monoclonal antibodies may be made by fusing immune B cells from the spleen of an immunized mouse with immortal cells to produce hybridomas specifically secreting each antibody, using art-known methods (e.g., Coligan et al., eds. *Current Protocols in Immunology*, John Wiley and Sons, 1992; Kohler et al., *Nature* 256:495, 1975; Hammerling et al., in *Monoclonal Antibodies and T Cell Hybridomas*, Elsevier, N.Y., 1981).

Uses of the invention

As a diagnostic

One application of the invention is as a diagnostic device to ascertain whether a patient has been exposed to *H. pylori* to a degree sufficient to mount an immune response. Use of current technology makes this aspect of the invention practical for clinical use in a short period of time, and has the advantage over existing tests for *H. pylori* infection that it requires only a simple withdrawal of blood from the patient.

EXAMPLE

Figure 2:
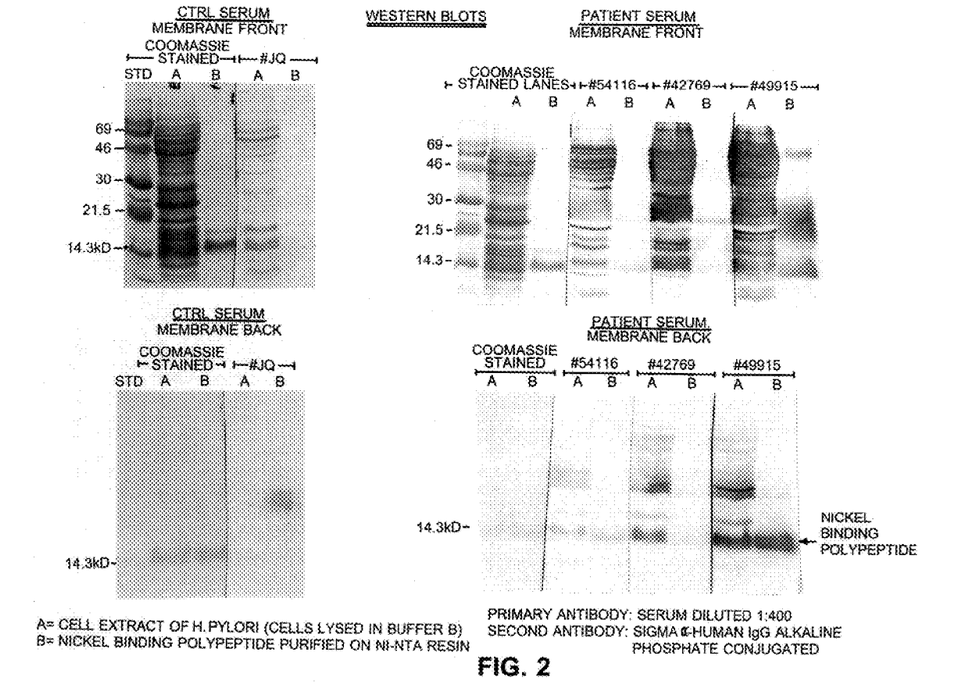
FIG. 2: Western blot of serum from patients infected with Helicobacter and controls of uninfected patients.

Serum was obtained from patients known to have an infection of *H. pylori* and from uninfected control patients. Purified nickel binding protein from *H. pylori* was immobilized on a membrane for Western Blot analysis (Sambrook et al., supra). Patient serum was diluted to 1:400 and tested on the Western blots of nickel binding protein. Antibodies to the nickel binding protein were identified in *H. pylori*-infected human serum by the Western blot analysis. Control serum reacted much more weakly, if at all (FIG. 2).

As a vaccine

The above example demonstrates that the nickel binding protein of *H. pylori* is antigenic during infection, and thus another use for this protein in the invention is as a vaccine against Helicobacter infection. The purified polypeptide or an antigenic epitope thereof can be admixed with a composition suitable for a vaccine (using techniques known in the art) and used to inoculate a patient, inducing an immunogenic response that would offer protection against an infection by *H. pylori*. Any portion of the polypeptide might be effective, especially those regions that are exposed when the protein is folded into its tertiary or quaternary configuration, and thus the nickel binding region is not necessarily the primary region of interest for this embodiment of the invention.

As a therapeutic

The protein of the invention might also serve as a means to scavenge free nickel ions in the body, either to treat an excess of such ions, as in nickel poisoning (often seen in industrial settings), or to compete with *H. pylori* to bind endogenously available nickel ions in the gastric mucosa. The nickel binding domain of the protein would be the only essential component, although larger fragments, up to and including the entire protein, would be acceptable.

Administered orally, the nickel binding polypeptide would have access to the gastric environment colonized by *H. pylori*, and would serve as a non-toxic competitor of the organism's own nickel scavenging mechanism. Since nickel is required for activity of the ureases, and urease activity (and its resulting ammonia production) is responsible for gastritis and peptic ulcers, insufficient free nickel would lead to inactive or weakly active ureases. This would have the effect of preventing or mitigating gastritis and peptic ulcers. To minimize digestion of the protein in the stomach, recombinant polypeptides could be made in which one or more peptide bonds have been replaced with an alternative type of covalent bond (a "peptide mimetic") which is not susceptible to cleavage by peptidases common in the stomach. Where proteolytic degradation of the peptides following administration to the subject is a problem, replacement of a particularly sensitive peptide bond with a non-cleavable peptide mimetic could result in a more stable peptide. Such mimetics, and methods of incorporating them into polypeptides, are well known in the art. Similarly, the replacement of an L-amino acid residue is a standard way of rendering the polypeptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benyxloxycarbonyl, fluorenylmethoxycarbonyl, methoxyazelayl, methoxyadipyl, methoxysuberyl, and 2,4,-dinitrophenyl. The latter approaches require synthesis of polypeptides rather than recombinant techniques.

Chelating and removing the nickel may have an additional protective effect on the mucosa. The protein-bound nickel ions may be a source of free radicals (for review, see Sunderman (1987) *Toxicological and Environmental Chemistry*, 15:59), which have well-known deleterious effects on cells, damaging nucleic acids, proteins, and lipids. Common dietary sources of nickel, such as coffee, tea, and chocolate, are thought to be irritating to patients with ulcers due to the formation of free radicals once they are ingested. Thus, the benefits of mitigating a free radical source of tissue damage, as well as the source of ammonia (active urease), are easily recognized.

An additional therapeutic use for the molecules of the invention can be as an antisense therapy. Antisense molecules can be made to any portion of the DNA of the invention using standard synthesis methods, and administered to a patient to mitigate gastric tissue damage by inhibiting the transcription and/or translation of the nickel binding protein of Helicobacter. Since the protein of interest is bacterial, a likely vector for the antisense molecule is a bacteriophage, which will preferentially infect bacteria and produce the desired antisense molecule. This treatment would not be deleterious to normal bacterial flora, since they (e.g., *E. coli*) do not produce the nickel binding protein. Additionally, vectors could be chosen from more standard viral and plasmid vector systems, or possibly the molecules could be administered without a vector, e.g., by oral administration, the bacteria would be directly exposed to the antisense molecule and could take it up via normal (e.g., phagocytic) mechanisms. The molecules would be administered to the patient in a suitable excipient using methods known in the art. Antisense molecules would be selected which bind to the DNA of the organism to inhibit transcription of the nickel binding gene or to the mRNA to prevent translation of the protein.

The nickel binding protein could also be used to identify and design drugs which interfere with *H. pylori* cells. For instance, a drug that interacts with the protein could preferentially bind to it instead of allowing nickel to bind, resulting in prevention of active urease assembly. Screening drugs for this facility would be relatively easy by establishing a competitive assay (as is standard in the art) between the test compound and nickel, and using purified protein or nickel binding fragments as the binding substrate. For example, the Ni-NTA Qiagen resin could be used as the source of nickel in the assay, and amount of protein adhering to the resin in the presence and absence of the test compound could be the measure of drug binding efficacy.

Environmental applications

An additional use for the polypeptide of the invention, or metal-binding fragments thereof, is as a purifying agent for aqueous solutions. There are many possible commercial and industrial applications for such decontamination methods. For example, such technology is well suited to waste management involving radioactive isotopes of nickel. Since it is desirable to reduce the volume of liquid radioactive waste whenever possible, a feasible use of the nickel binding protein is to mix soluble portions of the nickel binding polypeptide with the aqueous waste (after titrating the waste to an appropriate pH), allowing binding of the radioactive metal ion, and then removing the bound protein-metal complex from the solution (e.g., by immunoprecipitation, centrifugation, etc.). $^{63}Ni$ is an example of a radionuclide that can be removed by this method. Alternatively, a nickel binding polypeptide of the invention could be bound to a solid support (e.g., a resin, or larger support), then added to the solution to be decontaminated, and mixed so that the nickel would have access to the protein. Once the free nickel was bound, it would be a simple matter to remove the large support or centrifuge the resin to obtain a small volume of solid waste.

The method is also applicable for non-radioactive aqueous solutions, and can be used with any volume of liquid.

Deposit

Under the terms of the Budapest Treaty on the International Recognition of the Deposit of Microorganisms for the Purpose of Patent Procedure, deposit of plasmid pSKHP2-17 containing a 3.5 kb genomic clone with the sequence of the *Helicobacter pylori* nickel binding protein has been made on Jun. 7, 1994 with the American Type Culture Collection (ATCC) of Rockville, Md., USA where the deposit was given Accession Number 75806.

Applicants' assignees, New England Medical Center Hospital and Tufts University School of Medicine, represent that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. §122. The deposited material will be maintained with all the care necessary to keep it viable and uncontaminated for a period of at least five years after the most recent request for the furnishing of a sample of the deposited plasmid, and in any case, for a period of at least thirty (30) years after the date of deposit or for the enforceable life of the patent, whichever period is longer. Applicants' assignees acknowledge their duty to replace the deposit should the depository be unable to furnish a sample when requested due to the condition of the deposit.

What is claimed is:

1. An isolated antibody that specifically binds to a protein, wherein the protein:
   a) is found in Helicobacter bacteria,
   b) comprises the amino acid sequence of SEQ ID NO:1;
   c) has a monomeric molecular weight of about 14 kDa as determined by polyacrylamide gel electrophoresis; and
   d) is a nickel-binding protein.

2. A method of detecting a Helicobacter infection in a patient, said method comprising
   (a) obtaining a biological sample from a patient;
   (b) contacting said biological sample with antibodies specific for SEQ ID NO:1; and
   (c) detecting the formation of an antibody-antigen complex,
   wherein the presence of said complex indicates that said patient is infected with Helicobacter.

3. The antibody of claim 1, wherein the antibody is a monoclonal antibody.

4. The antibody of claim 1, wherein the antibody is a polyclonal antibody.

5. The method of claim 2, wherein the antibody is a monoclonal antibody.

6. The method of claim 2, wherein the antibody is a polyclonal antibody.

* * * * *